United States Patent [19]

Dirlam

[11] Patent Number: 4,584,385
[45] Date of Patent: Apr. 22, 1986

[54] ANTIBACTERIAL 2-AMINO-OXAZOLINONES AND PROCESS THEREFOR

[75] Inventor: John P. Dirlam, Gales Ferry, Conn.

[73] Assignee: Pfizer Inc., New York, N.Y.

[21] Appl. No.: 697,818

[22] Filed: Feb. 4, 1985

Related U.S. Application Data

[63] Continuation-in-part of Ser. No. 592,328, Mar. 22, 1984, abandoned.

[51] Int. Cl.$^4$ .................... C07D 263/08; A61K 31/42
[52] U.S. Cl. ................................. 548/225; 548/182; 548/184; 548/185; 548/233; 548/234; 548/238; 548/468
[58] Field of Search ................ 548/225, 233, 234, 238

[56] References Cited

U.S. PATENT DOCUMENTS

| | | | |
|---|---|---|---|
| 3,173,923 | 3/1965 | Rao et al. | 548/225 |
| 3,320,282 | 5/1967 | von Wittenau et al. | 548/225 |
| 4,049,816 | 9/1977 | Hardon et al. | 548/184 |

OTHER PUBLICATIONS von Wittenau et al., J. Amer. Chem. Soc., 85, 3425-3431, (1963).
von Wittenau et al., J. Amer. Chem. Soc., 83, 4678-4680, (1961).

Primary Examiner—George F. Lesmes
Assistant Examiner—S. A. Gibson
Attorney, Agent, or Firm—Charles J. Knuth; Peter C. Richardson; James H. Monroe

[57] ABSTRACT

A series of novel antibacterially active derivatives of indolmycin as well as some prodrug forms of indolmycin is disclosed. A novel process for the production of these compounds is also disclosed.

9 Claims, No Drawings

ANTIBACTERIAL 2-AMINO-OXAZOLINONES AND PROCESS THEREFOR

RELATED APPLICATIONS

This application is a continuation-in-part of pending application Ser. No. 592,328, filed Mar. 22, 1984, now abandoned.

BACKGROUND OF THE INVENTION

Indolmycin is an antibiotic substance first produced by fermentation from *Streptomyces albus* (U.S. Pat. No. 3,173,923) and later synthesized by Schach von Wittenau (*J. Am. Chem. Soc.* 83, 4678 (1961); ibid. 85,3425 (1963)). Related antibacterial compounds are taught in U.S. Pat. No. 3,320,282 and other related compounds having antiviral and antibacterial activities are taught in U.S. Pat. No. 4,049,816. It has now been discovered that a series of novel derivatives of indolmycin possess antibacterial activity, and that certain of these derivatives serve as prodrugs of the parent compound. A novel and highly advantageous process has also been discovered to produce indolmycin and these compounds.

SUMMARY OF THE INVENTION

The present invention comprises a series of novel compounds of the formula

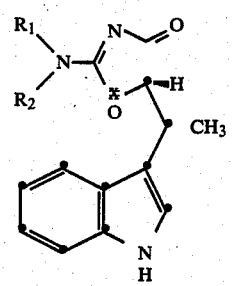

I wherein

R$_1$ is hydrogen or methyl with the proviso that when:
R$_1$ is hydrogen,
R$_2$ is C$_3$-C$_6$ cycloalkyl or mono-substituted alkyl having from about 1-4 carbon atoms wherein said substituent is selected from halogen, hydroxy, lower alkoxy, lower thioalkyl, aryl, or an unsaturated 2-4 carbon atoms side-chain; and when
R$_1$ is methyl,
R$_2$ is COR$_3$ wherein R$_3$ is alkyl or mono-substituted alkyl having from 1-4 carbon atoms, wherein said substituent is selected from amine, halogen, phenyl, p-hydroxyphenyl, or lower alkoxy; or amino substituted with C$_1$-C$_4$ alkyl, C$_3$-C$_6$ cycloalkyl or phenyl.

The following compounds are preferred:

A compound according to claim 1 wherein R$_1$ is hydrogen and R$_2$ is CH$_2$CH$_2$F;

A compound according to claim 1 wherein R$_1$ is hydrogen and R$_2$ is CH$_2$CH=CH$_2$;

A compound according to claim 1 wherein R$_1$ is hydrogen and R$_2$ is cyclopropyl;

A compound according to claim 1 wherein R$_1$ is H and R$_2$ is CH$_2$C≡CH;

A compound according to claim 1 wherein R$_1$ is methyl and R$_2$ is CH$_3$CO;

A compound according to claim 1 wherein R$_1$ is methyl and R$_2$ is CH$_3$CH$_2$CO;

A compound according to claim 1 wherein R$_1$ is methyl and R$_2$ is CH$_3$NHCO; and A compound according to claim 1 wherein R$_1$ is methyl and R$_2$ is PhNHCO and Ph is phenyl.

Another feature of the present invention is:

A process for the production of a compound of the formula:

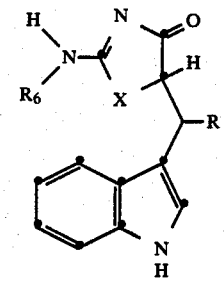

II which comprises: (a) contacting a compound of the formula:

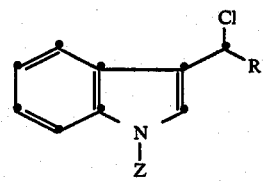

III with at least 2 equivalents of an anion derived from a compound of the formula:

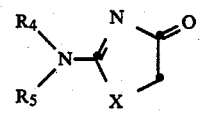

IV wherein
X is O, S or CH$_2$;
R is hydrogen or methyl
R$_4$ and R$_5$ are alkyl having from about 1-4 carbon atoms;
Z is CO$_2$CH$_2$Ph or CO$_2$C(CH$_3$)$_3$; and Ph is phenyl; and (b) further contacting the resulting intermediate with an amine of the formula R$_6$NH$_2$ wherein R$_6$ is alkyl having from 1-4 carbon atoms, C$_3$-C$_6$ cycloalkyl or mono-substituted alkyl having from about 2-4 carbon atoms wherein said substituent is selected halogen, hydroxy, lower alkoxy, lower thioalkyl, or an unsaturated 2-4 carbon atom side-chain.

The process is especially preferred wherein R$_6$ is methyl and X is either O, S or CH$_2$.

DETAILED DESCRIPTION OF THE INVENTION

The novel compounds of this case can be prepared by a variety of methods including the novel method to be discussed later in this specification. Whatever method is employed in preparing the compounds, it is critical to know that only the 5S,6R isomer of four possible stereoisomers, is biologically active. A mixture of isomers, however, has activity so long as it contains the active isomer.

In some of the methods for preparing the compounds of this invention, indolmycin itself is used as a reactant. In one such method indolmycin can be reacted with a desired anhydride such as propionic anhydride and acetic acid to achieve the desired product. In another such method indolmycin can be reacted with what may be called an "activated anhydride" such as the reaction product of mono-methylsuccinate, triethylamine and ethyl chloro-formate to achieve a desired product.

In yet another example of this type of preparation, indolmycin is reacted with a desired isocyanate, such as methyl isocyanate to achieve a desired product. Using this method or the above mentioned procedures, products are obtained wherein $R_2$ is $COR_3$. These compounds are hydrolyzable, and upon cleavage of the $COR_3$ side-chain afford indolmycin (i.e., prodrugs of indolmycin).

Indolmycin can also be used as a reactant in the preparation of novel compounds by its reaction with amines such as allyl amine or cyclopropyl amine followed by chromatographic separation to achieve the desired product. This reaction can be accomplished using a variety of solvents such as ethanol, methanol, water, acetonitrile, etc. However, in certain cases an optimum reaction mixture is obtained when the amine is used in excess (neat), without added solvent.

The novel process of this invention involves the preparation of one of the reactants, 2-dimethylamino-2-oxazolin-4-one (compound E). One method of obtaining this compound involves reacting glycolate and dimethyl cyanamide and another method involves reacting ethyl glycolate and guanidine followed by treatment with dimethylamine. Both of these method are illustrated in Scheme I.

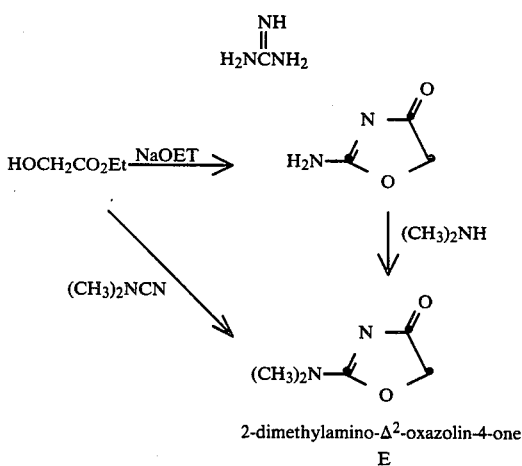

2-dimethylamino-$\Delta^2$-oxazolin-4-one
E

Armed with this reactant, one can proceed with the novel process of this invention to achieve the novel products. The novel process is illustrated in Scheme II.

Scheme II

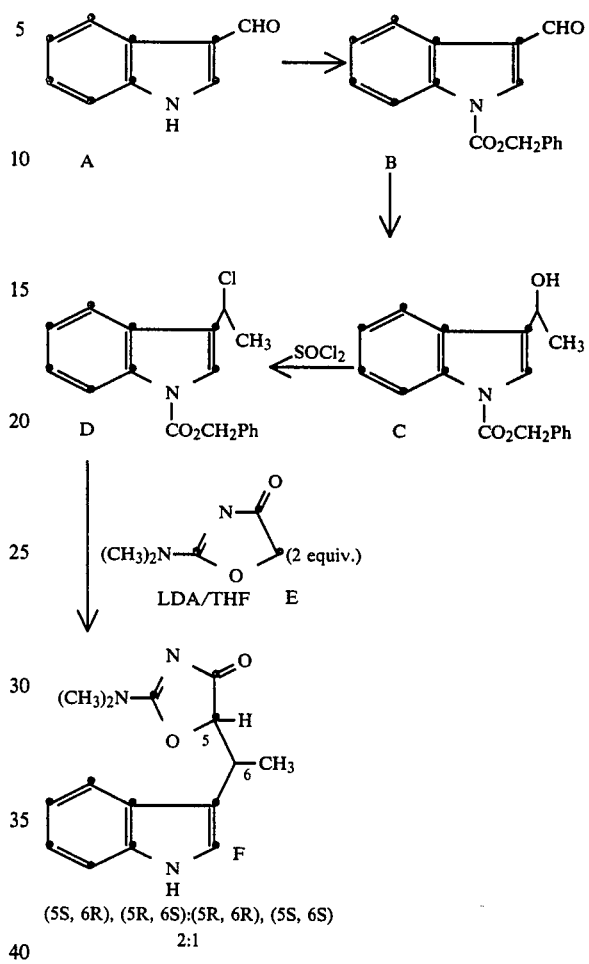

(5S, 6R), (5R, 6S):(5R, 6R), (5S, 6S)
2:1

Following Scheme II, one first reacts sodium hydride/benzyl chloroformate with compound A to obtain compound B. This material is reacted with methyl magnesium bromide to yield compound C.

Alternatively, compound C can be obtained from 3-acetyl indole, which is initially treated with sodium hydride/benzyl chloroformate. This reaction produces N-carbobenzoxy-3-acetyl indole which is then stirred with lithium aluminum hydride and ether to produce compound C.

Compound C is reacted with thionyl chloride to produce compound D. It is compound D which is now reacted with the anion of previously produced compound E (2 equivalents) to produce compound F (mixture of isomers), a novel compound of this invention. It will be apparent that although Scheme II is shown with methyl substituents on the amino side-chain of the oxazolinone ring, other substituents are allowed within the limits of the claimed invention. In these cases, additional diisopropylamide (LDA) base may be required due to deprotination of the amino-side chain.

Scheme III illustrates how a compound of Scheme II, following column chromatographic separation can be used to produce (±)-indolmycin by an amine exchange reaction.

Scheme III

Amine Exchange

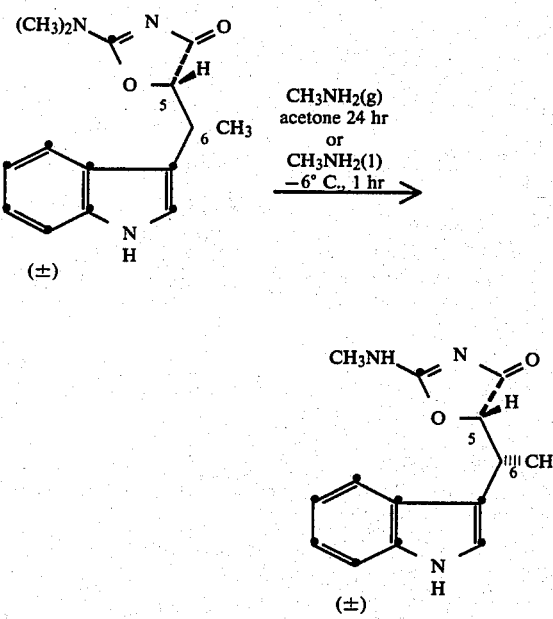

Yet another method of the novel process of this invention involves reacting compound G, formed from ethyl mercaptoacetate and dimethyl cyanamide in the presence of sodium hydride, with compound D to form compound H as a mixture of isomers. Treatment of compound H with methyl amine affords a mixture of isomers which has as the major component (±)-2-methylamino-5-[(3-indolyl)methyl]-2-thiazolin-4-one (I) (claimed in U.S. Pat. No. 4,049,816).

Scheme IV

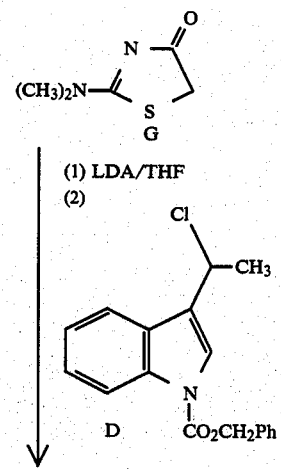

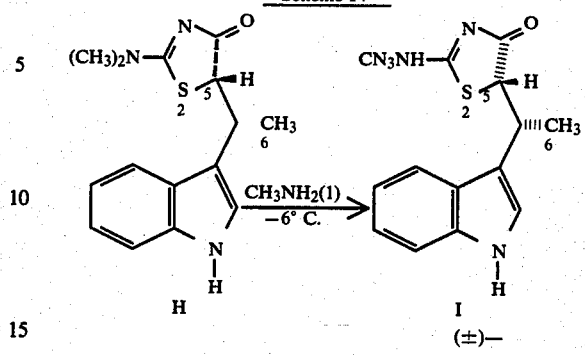

(5S,6R), (5R,6S):(5R,6R), (5S,6s) 5:1

The antibacterial compounds of the invention are active against gram-negative bacteria, and in particular they are active against Pasteurella spp., Haemophilus spp., Fusobacterium spp. and Mycoplasma spp. This in vitro antibacterial activity can be demonstrated by conventional two-fold serial dilution technique in Brain-Heart Infusion broth (Difco). The broth is inoculated with bacteria, and with the compounds of this invention, and then it is incubated overnight at 37° C., under anaerobic or aerobic conditions. On the next day, the test is read visually. The minimum inhibitory concentration (MIC) of test compound is the lowest concentration which prevents turbidity, i.e., which prevents growth of the microorganism. In vitro activities of certain of the compounds of the invention are shown in Tables I–V.

The compounds of this invention also show antibacterial activity in vivo. In determining such activity, the test compound is administered to mice which have been infected by intraperitoneal injection of a lethal inoculum of pathogenic bacteria. The test compound is administered using a multiple dosing regimen at a dosage of 50–200 mg/kg, and using either the oral (PO) or the subcutaneous (SC) route. The inoculum of bacteria varies from one to about ten times the amount needed to kill 100% of the mice, under conditions of the test. At the end of the test, the activity of a compound is assessed by counting the number of survivors among the treated animals and expressing the activity of a compound as the percentage of animals which survive. In most cases 50% protective dose value ($PD_{50}$) was calculated following additional testing by the probit method (H. E. Batson, "An Introduction to Statistics in the Medical Sciences," Burgess Publishing Co., Minneapolis, Minn., 1957, pp 64–69). In Tables I–V, in vivo activities of a number of compounds of this invention against *Pasteurella multocida, Pasteurella haemolytica, Haemophilus somnus,* and *Fusobacterium necrophorum.*

The in vivo activity of the compounds of this invention makes them useful for the treatment of bacterial infections, due to susceptible organisms, in animals, particularly swine, cattle and poultry. When used in animals for these purposes, the compounds can be administered orally or parenterally, i.e. intramuscularly, subcutaneously or intraperitioneally, at a dosage of from about 1 mg./kg. of body weight to about 100 mg./kg. of body weight. However, in general, it will be found that a dosage in the range from about 5 mg./kg. of body weight to about 50 mg./kg. of body weight will suffice. The compounds can be administered alone, or they can be combined with various diluents and carriers, according to standard veterinary practice.

When parenteral use of the compounds of this invention is contemplated, they can be combined with vehicles such as water, isotonic saline, isotonic dextrose, Ringer's solution, or non-aqueous diluents such as vegetable oils (cotton seed oil, sesame oil, corn oil) or dimethylsulfoxide. Buffering agents, local anesthetics and/or inorganic salts are commonly added to afford desirable pharmacological properties.

In the case of oral use, the compounds of this invention can be combined with various diluents including aqueous diluents. Non-aqueous diluents and solid diluents, in the form of capsules, tablets, lozenges, troches, dry mixes, suspensions, solutions and dispersions. They can also be blended with animal feed.

TABLE II

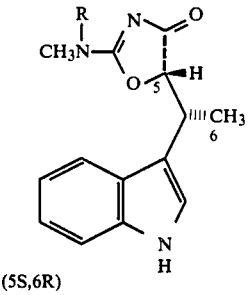

(5S,6R)

| R | IN VITRO | | | IN VIVO |
|---|---|---|---|---|
| | METHOD | µg/ml Haem. parahaem. | Past. mult. | PD$_{50}$, SC mg/kg Past. mult. |
| H (Indolmycin) | | 0.39–3.12 | 0.39 | |
| CONHCH$_3$ mp 184–185° | D | 25 | 1.56 | 30 (18)* |
| CONHCH$_2$CH$_2$CH$_2$CH$_3$ mp 110° | D | 6.25 | 3.12 | 30% protection at 50 mg/kg |
| CONHCH(CH$_3$)$_2$ | D | 25 | 3.12 | 21 (39)* |

TABLE I

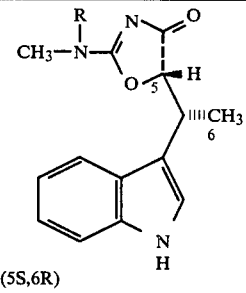

(5S,6R)

| R | IN VITRO | | IN VIVO |
|---|---|---|---|
| | METHOD | µg/ml Haem. parahaem. | Past. mult. | PD$_{50}$, SC mg/kg Past. mult. |
| H (Indolmycin) | | 0.39–3.12 | <0.39 | |
| COCH$_2$ mp 165° | A | 1.56 | <0.39 | 11 (32)* |
| COCH$_2$CH$_3$ mp 144–145° | A,C | — | <0.39 | 4 (13)* |
| COCH(CH$_3$)$_2$ mp 188–189° | B | 1.56 | <0.39 | 49 (18)* |
| COCH$_2$CH(CH$_3$)$_2$ oil | B | 3.12 | <0.39 | 21 (47)* |
| COCH$_2$CH$_2$CH$_2$N⟨piperidine⟩ mp 185–189° | C | 1.56 | <0.39 | 49 (18)* |
| CO—phenyl mp 157–164° | C | 0.78 | <0.39 | 3 (4)* |
| COCH$_2$CH$_2$—C$_6$H$_4$—OH mp 125–130° | C | 6.25 | 3.12 | 24 (13)* |

*Value obtained for indolmycin (positive control).

TABLE II-continued

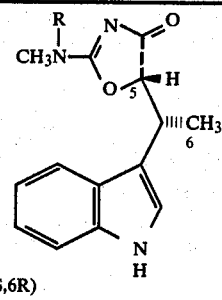

(5S,6R)

| R | METHOD | IN VITRO μg/ml Haem. para-haem. | Past. mult. | IN VIVO PD50, SC mg/kg Past. mult. |
|---|---|---|---|---|
| mp 145° | | | | |
| CONHC(CH3)3 mp 110–120° | D | 6.25 | 3.12 | 39 (4)* |
| CONH–cyclohexyl mp 134–135° | D | 1.56 | 6.25 | 16 (4)* |
| CONHCH2CO2Et mp 95–100° | D | 6.25 | 1.56 | 30% protection at 50 mg/kg |
| CONH–phenyl mp 145–146° | D | 1.56 | 0.39 | 5 (47)* |

*Value obtained for indolmycin (positive control).

TABLE III

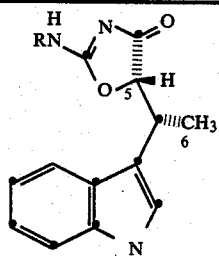

Natural form (as shown) = 5S,6R ISO form: 5R,6R

| R | METHOD | IN VITRO μg/ml Haem. para-haem. | Past mult. | IN VIVO PD50, SC mg/kg Past. mult. |
|---|---|---|---|---|
| H (Lit. cmpd.)* mp 203–206 (5S,6R; 5R,6R) | | — | 6.25 | 44 (18)* |
| CH3 (Indolmycin) | | 0.39–3.12 | 0.39 | |
| CH2CH2F mp 198–203 | F | — | 3.12 | 18 (47)* |
| CH2CH2OH mp 120° | F | >25 | 6.25 | 10% protection at 50 mg/kg |
| CH2CH=CH2 mp 166–168° | F | >25 | 12.5 | 11 (11)* |
| CH2C≡CH mp 70–80° | F | — | 50 | 22 (33)* |
| CH2CH2OCH3 mp 60–65° | F | >25 | 50 | 10% protection at 50 mg/kg |
| CH2CH2OCH2CH3 | F | >25 | 200 | 124 (35)* |

TABLE III-continued

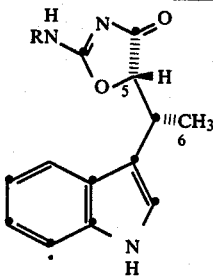

Natural form (as shown) = 5S,6R ISO form: 5R,6R

| R | METHOD | IN VITRO μg/ml Haem. para-haem. | Past mult. | IN VIVO PD50, SC mg/kg Past. mult. |
|---|---|---|---|---|
| mp 150–153° | | | | |
| CH2–piperidine mp 158–160° | F | — | 25 | NOT TESTED |
| CH2CH2N–morpholine mp 70–90° | F | >25 | 12.5 | NOT TESTED |
| CH2CH2CN mp 65–70° | F | — | 50 | NOT TESTED |
| CH2CH2SCH3 mp 161–163° (5S6R; 5R6R) | F | >25 | 25 | NOT TESTED |
| cyclopropyl mp 193–194° | F | 1.56 | 1.56 | 16 (11)* |
| cyclobutyl mp 130–135° | F | >25 | 25 | 50 (8)* |

*Value obtained for indolmycin (positive control).

TABLE IV

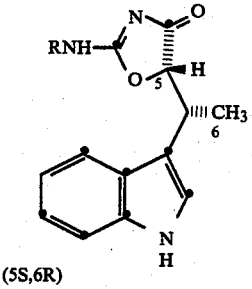

(5S,6R)

| R | IN VITRO μg/ml | | IN VIVO PD50,SC, mg/kg | | |
|---|---|---|---|---|---|
| | Past. haemo-lytica | Haemo-philus somnus | F. necro. | Past. haem. | Haemo-philus somnus |
| CH2CH=CH2 | 50–100 | 12.5 | 12.5–25 | 8.0 | 1.6 |

TABLE IV-continued

RNH—[oxazolinone structure with (5S,6R) configuration, CH3, indole]

(5S,6R)

| R | IN VITRO | | IN VIVO | | |
|---|---|---|---|---|---|
| | μg/ml | | PD50,SC, mg/kg | | |
| | Past. haemo- lytica | Haemo- philus somnus | F. necro. | Past. haem. | Haemo- philus somnus |
| [cyclopropyl] | 6.25-25 | 0.39 | 1.56 | 6.2 | 1.4 |
| CH2C≡CH | 100 | 6.25 | 6.25 | 6.7 | 1.8 |
| CH2CH2F | 1.56-12.5 | 1.56 | 3.12 | 4.5 | 2.0 |

TABLE V

CH3NH—[oxazolinone structure with X, CH3, indole]

| | IN VITRO | IN VIVO |
|---|---|---|
| | μg/ml Past. mult. | % Protection @ 200 mg/kg. SC Past. mult. |
| X | | |
| O   Indolmycin | 0.39 | 100 |
| CH2  (±)-mixture | 12.5 | 90 |

In the description above and in the illustrative examples to follow the following general remarks can be made. Melting points (uncorrected) were taken with a Thomas-Hoover capillary apparatus. NMR spectra were recorded on Varian A-60 and T-60 spectrometers or a Brooker W. M. −250 instrument with Me4Si as an internal standard. IR spectra were determined with a Perkin Elmer Model 21 spectrophotometer; UV spectra were recorded on a Cary Model 14 spectrophotometer; optical rotations were measured with a Perkin Elmer Model 141 polarimeter; and mass spectra were obtained with a Perkin-Elmer RMU-6E mass spectrometer. Micro-analyses were performed by the Pfizer Analytical Department. All evaporations were conducted in vacuo using either a water aspirator or a vacuum pump.

EXAMPLE 1

(Method A)

(−)-(5S,6R)-2-[N-Propionyl-N-methyl]amino-5-[1-(indol-3-yl)ethyl]-Δ²-oxazolin-4-one A mixture of indolmycin (2.57 g, 10 mmol) in propionic anhydride (25 ml) and acetic acid (5 ml) was heated at 50° for 30 min. The mixture was evaporated in vacuo to afford an oil residue. Following trituration with ether, the residue crystallized to give the desired product (1.05 g, 34% yield), m.p. 144°-145°.

EXAMPLE 2

(Method B)

(−)-(5S,6R)-2-(N-iso-Butyryl-N-methyl)amino-5-[1-(indol-3-yl)ethyl]-Δ²-oxazolin-4-one A mixture of indolmycin (2.57 g, 10 mmol), isobutyric anhydride (5 ml) and p-dimethylaminopyridine (25 mg) was stirred at room temperature for 20 hrs. The reaction mixture was poured into water (500 ml) and was extracted with ethyl acetate (2×100 ml). The combined ethyl acetate extract was washed with water (2×), and a saturated sodium chloride solution (1×), and dried over anhydrous sodium sulfate. The solvent was removed to afford a residue that was triturated with ether (2.8 g, 86% yield), m.p. 188°-189° C.

EXAMPLE 3

(Method C)

(−)-(5S,6R)-2-[N-(2-Methoxypropionyl)-N-methyl-]amino-5-[1-(indol-3-yl)ethyl]-Δ²-oxazolin-4-one To a solution of mono-methylsuccinate (2.64 g, 20 mmol) in tetrahydrofuran (50 ml) at −10° was added triethylamine (4.04 g, 40 mmol). The reaction mixture was stirred for 5 min. and then ethyl chloroformate (2.16 g, 20 mmol) was added dropwise over a 5 min. period. The resulting mixture was stirred at −10° for 30 min. and was then cooled to −30° and indolmycin (2.57 g, 10 mmol) was added. The mixture was allowed to warm to room temperature and was stirred for an additional hour. The triethylamine hydrochloride salt was removed by filtration and the filtrate was evaporated in vacuo to an oil. The resulting oil was taken up in ethyl acetate and was washed first with water, then with saturated sodium bicarbonate solution, and again water and was then dried over anhydrous sodium sulfate. The solvent was evaporated in vacuo to afford the desired product as an oil (2.80 g, 73% yield).

EXAMPLE 4

(Method D)

(−)-(5S,6R)-2-[N-(N'-Methylcarbamoyl)-N-methylamino]-5-[1-(indol-3-yl)ethyl]-Δ²-oxazolin-4-one To a suspension of indolmycin (2.57 g, 10 mmol) in methylene chloride (35 ml) was added excess methyl isocyanate (2.85 g, 50 mmol) in methylene chloride (15 ml) with cooling. The reaction mixture was allowed to stir overnight at room temperature. The mixture was evaporated in vacuo and the residue was triturated with ether to afford the desired product in nearly quantitative yield (3.2 g), m.p. 184°-185° C.

EXAMPLE 5

2-n-Propylamino-5-[1-(indol-3-yl)ethyl]-Δ²-oxazolin-4-one (5S,6R; 5R,6S) (Method E)

To a mixture of 2-amino-5-[1-(indol-3-yl)ethyl]-Δ²-oxazolin-4-one (5S,6R; 5R,6S) (0.80 g, 3.3 mmol) in acetonitrile (2 ml) was added n-propylamine (0.30 g, 5.0 mmol). The reaction mixture was heated with a 75° C. oil bath for 17.5 m. An addition 0.5 g of n-propylamine was added and heating was continued for 10 hr. longer. The mixture was concentrated in vacuo and the residue was dissolved in acetone (1.5 ml) and was chromatographed on a silica gel 60 (90 g, 230–400 mesh) column with 1.5% methanol:chloroform (v:v) using a medium pressure pump. The desired product was obtain as a mixture of enantiomers (5S,6R; 5R,6S): 0.36 g (38% yield), mp 144°–146° (from ETOAC).

EXAMPLE 6

2-Allylamino-5-[1-(indol-3-yl)ethyl]-Δ²-oxazolin-4-one (5S,6R) (Method F)

A. To a slurry of indolmycin (12.0 g, 0.946 mol) in absolute ethanol (60 ml) was added allyl amine (15.2 g, 0.27 mol). The reaction mixture was heated under reflux for 17 hr. The mixture was concentrated in vacuo to afford an oil. TLC analysis of the oil indicated the presence of both diastereomers. Ethyl acetate (100 ml) was added to the oil and after 4 days a solid 7.2 g was separated from the mixture. This material was mainly the undesired diastereomer (5R,6R). The filtrate was concentrated in vacuo to afford 5.2 g of material that was then dissolved in N,N-dimethylformamide (5 ml) and chromatographed on a silica gel 60 (390 g, 230–400 mesh) column with 1% methanol:chloroform (v:v) using a medium pressure pump. The desired product (2.57 g, 20% yield) was obtained as a pure material: mp 166°–168° C.

Anal. Calcd. for $C_{16}H_{17}N_3O_2$: C, 67.84; H, 6.00; N, 14.84. Found: C, 67.92; H, 6.06; N, 14.95.

B. Indolmycin (10.0 g, 0.039 mol) was dissolved in 150 ml of allylamine in a 250 ml 3-necked round-bottomed flask fitted with a condenser, nitrogen inlet and a magnetic stirrer. The reaction was brought to reflux and refluxed overnight (16 hrs). The reaction was allowed to cool to room temperature, then the solvent was evaporated off leaving an off-white foam. This foam was dissolved in CHCl₃, then the CHCl₃ was evaporated off, until there was no odor of amine remaining (total of two times). The foam was dissolved in CHCl₃ with stirring and allowed to stand at room temperature for several days. The product was collected by filtration and washed with CHCl₃ and dried to afford 8.6 g of product (78% yield): mp 155°–161° C. The 250 MHz NMR indicates that the product is mainly the natural isomer (≦5% 5R,6R isomer is present). Pure material was obtained following column chromatography on a silica gel column.

EXAMPLE 7

2-Cyclopropylamino-5-[1-(indol-3-yl)ethyl]-Δ²-oxazolin-4-one (5S,6R) (Method F)

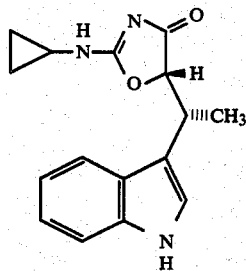

A. To a slurry of indolmycin (10.0 g, 0.039 mol) in absolute ethanol (30 ml) was added cyclopropyl amine (33.6 g, 0.58 mol). The reaction mixture was allowed to stir at room temperature for 7 days, and was then concentrated in vacuo leaving a yellow oil (13.5 g). TLC analysis of the oil indicated the presence of both diastereomers. The oil was dissolved in methanol and was chromatographed on a silica gel 60 (700 g, 230–400 mesh) column with 0.5–1% methanol:chloroform (v:v). The desired product (3.0 g, 27% yield) was obtained as a pure material: mp 193°–194° C.

Anal. Calcd. for $C_{16}H_{17}N_3O_2$: C, 67.84; H, 6.00; N, 14.84. Found: C, 67.18; H, 6.27; N, 14.39.

B. Indolmycin (10.0 g, 0.039 mol) was dissolved in 50 gm of cyclopropylamine in a 250 ml three-necked round-bottomed flask fitted with a condenser, a nitrogen inlet and a magnetic stirrer. The reaction was brought to reflux and refluxed overnight (16 hr.). The reaction was allowed to cool to room temperature and most of the solvent distilled off under vacumn. The remaining reaction mixture was evaporated to a foam, then dissolved in CHCl₃ and evaporated to a foam again. This was repeated until the odor of amine was gone. The foam was dissolved in CHCl₃, allowed to stand overnight and the precipitate collected by filtration 24 hrs. later and dried to afford 4.85 g (43% yield): mp 174°–181° C. The 250 MHz NMR indicates that the product is mainly the natural isomer (≦5% 5R,6R isomer is present). Pure material was obtained following chromatography on a silica gel column.

EXAMPLE 8

2-Dimethylamino-Δ²-oxazolin-4-one

A. To a stirred slurry of sodium hydride (0.96 g., 50% in oil, 20 mmol., extracted with hexanes) in toluene (100 ml.) under nitrogen at room temperature was added ethyl glycolate (9.60 ml., 100 mmol.). When hydrogen evolution ceased, dimethyl cyanamide (8.07 ml, 100 mmol) was added, and the mixture was heated to 87° C. for 1 hr. It was then cooled to room temperature, the solvent was evaporated, and the residue was refluxed with vigorous stirring in ethyl acetate (100 ml). This was filtered (hot), and the filtrate was evaporated to afford 5.30 g (41%) of the desired compound. Refluxing the insoluble material from above in ethyl acetate (100 ml), filtering, and evaporating the filtrate provided an additional 9% (1.15 g) of product; mp 106°–107°; NMR (Me₂SO-d₆) δ 3.03 (3, s, NCH₃), 3.10 (3, s, N—CH₃), 4.62 (2, s, H-5); Anal. Calcd. for $C_5H_8N_2O_2$: C, 46.92; H, 6.30; N, 21.89. Found: C, 47.04; H, 6.21; N, 21.79.

B. To 200-ml of absolute ethanol under a nitrogen atmosphere cooled with an ice-bath was added 11.6 g (0.51 mol) of sodium at 0° C. with stirring. The ice-bath was removed and the sodium was allowed to dissolve completely. Guanidine hydrochloride (46.1 g, 0.48 mol) was added and the reaction mixture was stirred for 1 hr. The resulting sodium chloride precipitate was removed by a suction filtration through supercel under nitrogen. Ethyl glycolate (50.2 g, 0.48 mol) was added to the reaction mixture dropwise over 1 hr. and the mixture was allowed to stir overnight at room temperature. The desired 2-amino-Δ²-oxazolin-4-one (42.3 g, 88%) was collected by filtration and triturated with ethanol and then with diethylether: mp 245°–246° C. 2-Amino-Δ²-oxazolin-4-one (5.0 g, 50 mmol) was slurried in ethanol (100 ml) at 60° C. Dimethyl amine gas was slowly bubbled into the reaction mixture for 2 hr. The solvent was removed under vacuum to afford 5.2 g (81%), of product as a white solid: mp 106°–107° C.

EXAMPLE 9

N-Carbobenzoxy-indole-3-carboxaldehyde

Sodium hydride (1.99 g, 50% in oil, 41.4 mmol, extracted with hexanes) was stirred in THF (50 ml) in a flame-dried flask at 0° C. under nitrogen. Indole-3-carboxaldehyde (5.00 g, 34.5 mmol) was added as a powder in small portions, and then the mixture was warmed to 40° C. for 30 min. The mixture was again cooled to 0° C., and benzyl chloroformate (4.92 ml, 34.5 mmol) was added. After warming to room temperature and stirring overnight, the mixture was poured into water (50 ml) and extracted with CH$_2$Cl$_2$ (50 ml). The organic layer was washed with water (50 ml), dried with MgSO$_4$, filtered and evaporated to 9.2 g (95%) of a gold-brown oil. Crystallization from hot hexane gave 8.47 g (88%) of white crystalline product: mp 70°–71° Anal. Calcd for C$_{17}$H$_{13}$NO$_3$: C, 73.19; H, 4.70; N, 5.02. Found: C, 72.79; H, 5.16; N, 5.24.

EXAMPLE 10

1-(N-Carbobenzoxy indol-3-yl)ethanol

A. To N-carbobenzoxy-indole-3-aldehyde (4.03 g, 14.4 mmol) in THF (50 ml) in a flame-dried flask under nitrogen at −78° C. was added methyl magnesium bromide (7.2 ml, 3.0M in ether, 21.7 mmol). After stirring 2 hrs at −78° C., the reaction was quenched (cold) with 30 ml 10% NH$_4$Cl solution. The mixture was extracted with CHCl$_3$ (2×45 ml), dried with MgSO$_4$, filtered and evaporated to afford 4.3 g (100% crude) of gold oil. Purification by column chromatography on silica gel (CHCl$_3$/EtOAc 4:1) gave 3.62 g (85%) of white solid: mp; 78°–80° C.; Anal. Calcd for C$_{18}$H$_{17}$NO$_3$: C, 73.29; H, 5.81; N, 4.75. Found: C, 73.28; H, 5.82; N, 4.70.

B. Lithium aluminum hydrode (1.2 g, 32 mmol) was suspended in tetrahydrofuran (100 ml) and cooled to −78° C. N-Carbobenzoxy-3-acetyl indole (19.3 g, 66 mmol) dissolved in tetrahydrofuran (200 ml) was added over 0.5 hr. and the reaction mixture was allowed to stir at −78° C. for 0.5 hr and then at 0° C. for 0.5 hr. Ether (300 ml) was added and the mixture was quenched with 1.2 ml H$_2$O, 1.2 ml 2N NaOH, adn 3.6 ml and H$_2$O. The mixture was filtered through celite, dried over MgSO$_4$ and evaporated leaving a solid. The solid was dissolved in 50 ml hot ether and then hexane was added (300 ml). The resulting crystals were collected to afford 12.5 g (64% yield): mp 79°–80° C., which was identical with the material prepared above in procedure A.

EXAMPLE 11

N-Carbobenzoxy-3-acetyl indole

To a stirred slurry of sodium hydride (3.77 g, 50% in oil, 7.86 mmol, extracted with hexanes) in THF (30 ml) at 0° C. under nitrogen was added dropwise 3-acetyl indole (10.0 g, 62.9 mmol) in THF (15 ml). After warming to room temperature and stirring one hour, the mixture was cooled to 0° C. and benzyl chloroformate (8.97 ml, 62.9 mmol) was added dropwise. The reaction was allowed to warm to room temperature and stir overnight. The excess sodium hydride was destroyed at 0° C. with 40 ml H$_2$O. The mixture was then extracted three times with CHCl$_3$ (total volume 120 ml), dried with MgSO$_4$, filtered and evaporated to an off-white solid. Recrystallization from hexanes afforded 15.85 g (86%) of product: mp 112°–113°; Anal. Calcd for C$_{18}$H$_{15}$NO$_3$: C, 73.79; H, 5.16; N, 4.78. Found: C, 73.86; H, 5.29; N, 4.95.

EXAMPLE 12

N-Carbobenzoxy-3-(1-chloroethyl)indole

To a stirred solution of 1-(N-carbobenzoxy indol-3-yl)ethanol (1.02 g, 3.45 mmol) in CH$_2$Cl$_2$ (20 ml) at −78° C. under nitrogen was added thionyl chloride (0.63 ml, 8.62 mmol). After warming to room temperature and stirring for 2 hrs, the mixture was evaporated to a brown oil. This was dissolved in CHCl$_3$, treated with activated carbon and filtered through a pad of Super Cel; the filtrate was evaporated to give 1.03 g (95%) of light brown oil: NMR (CDCl$_3$) δ 1.90 (3, d, CH$_3$), 5.26 (1, q, CHCl), 5.33 (2, s, PhCH$_2$), 7.20–7.85 (9, m, aromatic H's) 8.04 ppm (1, m, H-7̄). This material was relatively unstable, and therefore was used immediately without further purification (e.g., as in Example 13).

EXAMPLE 13

2-Dimethylamino-5-[1-(indol-3-yl)ethyl]-Δ$^2$-oxazolin-4-one

To 20 ml THF in a flame-dried flask under nitrogen at 0° C. was added diisopropylamine (0.94 ml, 6.70 mmol), followed by a n-butyl lithium 3.2 ml, 2.1M in hexane, 6.70 mmol). The mixture was cooled to −78° C., and 2-dimethylamino-Δ$^2$-oxazolin-4-one (0.86 g, 6.70 mmol) was added as a finely ground solid. After warming to room temperature and stirring for 105 min, the reaction was cooled to −78° C. and N-carbobenzoxy-3-(1-chloroethyl)indole (1.05 g, 3.35 mmol) was added in THF (5 ml). The mixture was warmed to room temperature and stirred overnight. Water (20 ml) was added, and the mixture was extracted with ethyl acetate (3×20 ml), dried with MgSO$_4$, filtered and evaporated. The crude product was subjected to medium pressure liquid chromatography on silica gel (3% MeOH/CHCl$_3$), and the less polar component was collected to afford 0.43 g (47%) of desired product (racemic mixture: 5S6R;5R6S). NMR(Me$_2$SO-d$_6$) δ 1.35 (3, d, CH$_3$), 2.97 (3, s, NCH$_3$), 3.02 (3, s, NCH$_3$), 3.76 (1, m, H-6), 4.93 (1, d, H-5), 6.77–7.75 (5, m, Ind-H), 8.37 (1, s(broad), NH).

The pure 5S,6R enantiomer was prepared by stirring (−)-indolmycin (obtained from fermentation) in 40% aqueous dimethylamine at room temperature overnight. The evaporated reaction mixture was subjected to medium pressure chromatography on silica gel (2% MeOH/CHCl$_3$) and recrystallized from Et$_2$O/i-PrOH to give the 5S,6R product: mp 149°–150° C., [α]$_D^{25}$=−175° (c=0.146, MeOH). Anal. Calcd for C$_{15}$H$_{17}$N$_3$O$_2$: C, 66.48; H, 6.32; N, 15.51. Found: C, 66.03; H, 6.33; N, 15.33. The NMR spectrum of this compound was identical to that of the racemic material prepared above.

EXAMPLE 14

(±)-2-Methylamino-5-[1-(indol-3-yl)ethyl]-Δ$^2$-oxazolin-4-one

Methylamine (5 ml) was condensed into a flask (equipped with Dry Ice/acetone condenser and stirring) containing (±)-2-dimethylamino-5-[1-(indol-3-yl)ethyl]-Δ$^2$-oxazolin-4-one (23 mg, 0.085 mmol) under nitrogen at −78° C. The cold bath was removed and the methylamine solution was allowed to warm to its boiling point (−6° C.) and stir for 1 hr. The condenser was then removed and the solvent evaporated, leaving 22 mg. (99%) of (±)-indolmycin. The spectral properties of this sample were identical to those of indolmycin from fermentation. No epimerization at C-5 was detected under these reaction conditions (i.e. no (±)-isoindolmycin was formed).

EXAMPLE 15

2-Dimethylamino-Δ²-thiazolin-4-one

To a stirred slurry of sodium hydride (144 mg, 50% in oil, 3 mmol, extracted with hexanes) in toluene (20 ml) under nitrogen at room temperature was added ethyl mercaptoacetate (1.64 ml, 15 mmol). When hydrogen evolution ceased, dimethyl cyanamide (1.21 ml, 15 mmol) was added, and the mixture was heated to 88° C. Within 5 min the color darkened through red to dark brown. After 1 hr, the reaction was cooled to room temperature, the solvent was evaporated, and the residue was refluxed with vigorous stirring in ethyl acetate (35 ml). This was filtered (hot), and the pale yellow filtrate was evaporated to afford 2.13 g. (98%) of yellow oil; this was crystallized from ethyl acetate/ether to afford 1.47 g (68%) of pale yellow crystals: mp 78°–80° C.; NMR (CDCl$_3$) δ 3.13 (3, s, NCH$_3$), 3.30 (3, s, NCH$_3$), 3.90 (2, s, H-5).

Anal. Calcd for C$_5$H$_8$ON$_2$S: C, 41.71; H, 5.60; N, 19.45; S, 22.27. Found: C, 41.60; H, 5.47; N, 19.08; S, 22.13.

EXAMPLE 16

2-Dimethylamino-5-[1-(indol-3-yl)ethyl]-Δ²-thiazolin-4-one (5S,6R; 5R,6S)

To 20 ml. THF in a flame-dried flask under nitrogen at 0° C. was added diisopropylamine (1.06 ml, 7.59 mmol), followed by n-butyl lithium (3.3 ml, 2.3M in n-hexane, 7.59 mmol). The mixture was cooled to −78° C., and 2-dimethylamino-Δ²-thiazolin-4-one (0.99 g, 6.90 mmol) was added as a finely ground solid. After warming to room temperature and stirring for 1 hr. the reaction was cooled to −78° C. and N-carbobenzoxy-3-(1-chloro-ethyl)indole (1.08 g, 3.45 mmol) was added in THF (5 ml). The mixture was warmed to room temperature and stirred overnight. Water (20 ml) was added, causing precipitation of a light yellow solid. This was removed by filtration, and the filtrate was extracted three times with a total of 60 ml of ethyl acetate, dried with MgSO$_4$, and evaporated to a gold-brown oil. This was subjected to column chromatography on silica gel (2% MeOH/CHCl$_3$) to afford 0.57 g (58%) of product: mp 243°–244° C. dec; NMR (Me$_2$SO-d$_6$)δ1.21 (3, d, CH$_3$), 3.10 (3, s, NCH$_3$), 3.20 (3, s, NCH$_3$), 3.86 (1, m, H-6), 4.83 (1, d, H-5), 6.82–7.83 (5, m, Ind-H), 10.90 (1, s(broad), NH).

EXAMPLE 17

2-Methylamino-5-[1-(indol-3-yl)ethyl]-Δ²-thiazolin-4-one (5S6R,5R6S; 5S6S,5R6R)

Methylamine (3 ml) was condensed into a flask (equipped with Dry Ice/acetone condenser) containing 2-dimethylamino-5-[1-(indol-3-yl)ethyl]-Δ²-thiazolin-4-one (21 mg, 0.073 mmol) under nitrogen at −78° C. The cold bath was removed, and the methylamine solution was allowed to warm to its boiling point (−6° C.) and stir for several hours. The condenser was then removed and the solvent evaporated, leaving 18 mg of a 3:1 mixture of isomers (5S6R,5R6S: 5S6S,5R6R, respectively, based on NMR and TLC analysis of the sample).

EXAMPLE 18

5-Dimethylamino-Δ¹⁽⁵⁾-pyrrolin-2-one

The crystalline imino ether hydrochloride prepared from ethyl 3-cyano-propionate (33.3 mmol, 7.0 g) was suspended in ethanol (30 mL) and cooled to 0° C. Anhydrous dimethyl amine was bubbled into the reaction mixture in a steady stream for 1 h. The homogeneous solution was stirred at room temperature for 20 hr. and the solvent was removed in vacuo. The residue was dissolved in 10% methanol/chloroform and filtered through a short column of silica gel to remove dimethylamine hydrochloride to afford 3.7 g (87%) of product: mp 117°–119° C., $^1$H-NMR (CDCl$_3$) δ 2.5–2.9 (2H, m), 3.1 (3H,s) 3.2 (3H,s).

EXAMPLE 19

5-Dimethylamino-3-[1-(indol-3-yl)ethyl]-Δ¹⁽⁵⁾-pyrrolin-2-one

5-Dimethylamino-Δ¹⁽⁵⁾-pyrrolin-2-one (1.0 g, 8.0 mmol) was suspended in tetrahydrofuran (20 mL) and cooled to −78° C. Lithium diisopropylamide (8.0 mmol, 16 mL of 0.5M solution) was added dropwise over 10 min and the reaction mixture was stirred for an addition 0.5 hr. N-Carbobenzoxy-3-(1-chloroethyl)indole (1.25 g 4.0 mmol) dissolved in tetrahydrofuran (10 mL) was added over 10 min and the reaction was stirred at −78° C. for 1 h and at room temperature for 4 h. Water (50 mL) was added and the mixture was extracted with ethyl acetate (2×100 mL). The combined organic layers were wash with saturated NaCl, dried (MgSO$_4$), and the solvent was removed in vacuo. The crude residue was purified on silica gel using 5% methanol/chloroform as eluent to afford 225 mg (20%) of product which appeared to be a 3:1 mixture of diastereomers by $^1$H-NMR.

EXAMPLE 20

3-[1-(Indol-3-yl)ethyl]-5-methylamino-Δ¹⁽⁵⁾-pyrrolin-2-one

This product was obtained using the conditions described in Example 14 starting with racemic 5-dimethylamino-3-[1-(indol-3-yl)ethyl]-Δ¹⁽⁵⁾-pyrrolin-2-one (mixture of diastereomers). The desired product (racemic mixture) was obtained following purification on silica gel using 10% methanol/chloroform as eluent: $^1$H-NMR (Me$_2$SO-d$_6$)δ 1.0 (3H, d), 2.4 (2H, d), 2.7 (3H, s), 3.2–3.6 (2H, m), 6.6–7.5 (5H, m), 8.4 (1H, s); mass spectrum m/e 255.1325 (m+; C$_{15}$H$_{17}$N$_3$O requires 255.1368).

I claim:
1. A compound of the formula:

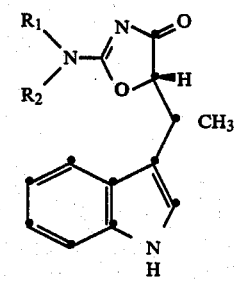

I wherein
- $R_1$ is hydrogen or methyl with the proviso that when:
- $R_1$ is hydrogen,
- $R_2$ is $C_3$-$C_6$ cycloalkyl or mono-substituted alkyl having from about 1–4 carbon atoms wherein said substituent is selected from halogen, hydroxy, lower alkoxy, lower thioalkyl, or alkenyl or alkynyl of 2–4 carbon atoms; and when
- $R_1$ is methyl,
- $R_2$ is $COR_3$ wherein $R_3$ is alkyl or mono-substituted alkyl having from 1–4 carbon atoms, wherein said substituent is selected from amine, halogen, phenyl, p-hydroxyphenyl, or lower alkoxy; or amino substituted with $C_1$-$C_4$ alkyl, $C_3$-$C_6$ cycloalkyl or phenyl.

2. A compound according to claim 1 wherein $R_1$ is hydrogen and $R_2$ is $CH_2CH_2F$.

3. A compound according to claim 1 wherein $R_1$ is hydrogen and $R_2$ is $CH_2CH=CH_2$.

4. A compound according to claim 1 wherein $R_1$ is hydrogen and $R_2$ is cyclopropyl.

5. A compound according to claim 1 wherein $R_1$ is H and $R_2$ is $CH_2C\equiv CH$.

6. A compound according to claim 1 wherein $R_1$ is methyl and $R_2$ is $CH_3CO$.

7. A compound according to claim 1 wherein $R_1$ is methyl and $R_2$ is $CH_3CH_2CO$.

8. A compound according to claim 1 wherein $R_1$ is methyl and $R_2$ is $CH_3NHCO$.

9. A compound according to claim 1 wherein $R_1$ is methyl and $R_2$ is $PhNHCO$.

* * * * *